[19] United States Patent
Aburada et al.

[11] Patent Number: 4,613,591
[45] Date of Patent: Sep. 23, 1986

[54] ADMINICULUM FOR ANTITUMOR AGENTS

[75] Inventors: Masaki Aburada; Shigefumi Takeda, both of Kawasaki; Eiko Itoh, Nagareyama; Moe Matsushita, Machida; Eikichi Hosoya, Tokyo, all of Japan

[73] Assignee: Tsumura Juntendo Inc., Tokyo, Japan

[21] Appl. No.: 509,197

[22] Filed: Jun. 29, 1983

[30] Foreign Application Priority Data

Aug. 23, 1982 [JP] Japan ............................. 57-144630

[51] Int. Cl.[4] ............................................ A61K 31/71
[52] U.S. Cl. ........................................ 514/34; 514/28
[58] Field of Search ............... 424/180; 536/18.1, 128, 536/6.4; 514/25, 28, 34

[56] References Cited

U.S. PATENT DOCUMENTS 3,940,381  2/1976  Boissevain ........................ 536/18.1
4,361,697  11/1982  Dobberstein et al. ............. 536/128

OTHER PUBLICATIONS

Nishizawa et al., *Chemical Abstracts* vol. 94, (1981), p. 357, No. 52764n.
Oshio et al., *Chemical Abstracts* vol. 96, (1982), p. 390, No. 196541b.

*Primary Examiner*—Johnnie R. Brown
*Assistant Examiner*—Elli Peselev
*Attorney, Agent, or Firm*—Ladas & Parry

[57] ABSTRACT

Adminiculum increasing the antitumor activities of mitomycin C and doxorubicin hydrochloride and decreasing the side effects associated with their use comprising an aqueous or aqueous organic solvent extract of a crude preparation of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix, a method for preparing said adminiculum and a method for its use. In addition, compositions and methods for treating tumor-bearing patients are disclosed.

14 Claims, 13 Drawing Figures

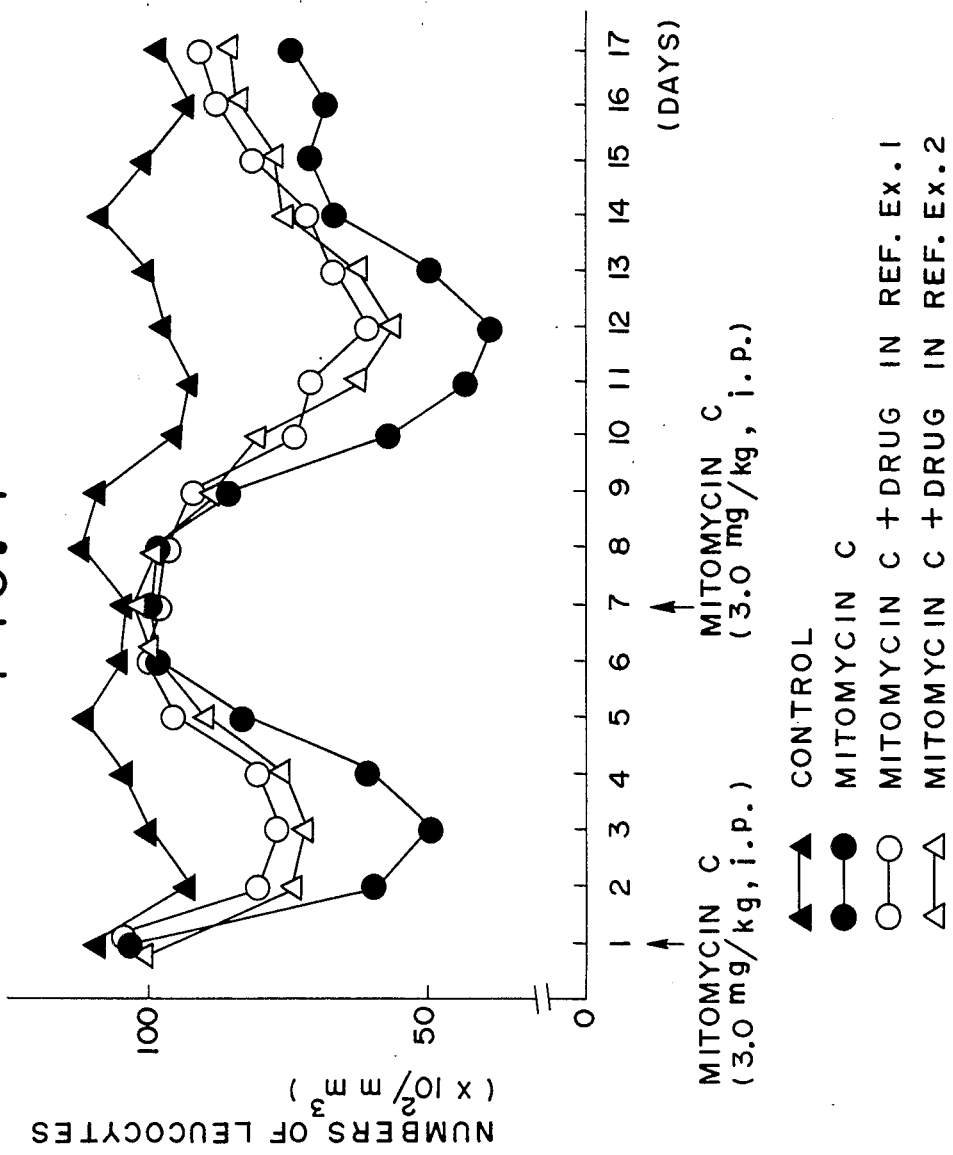

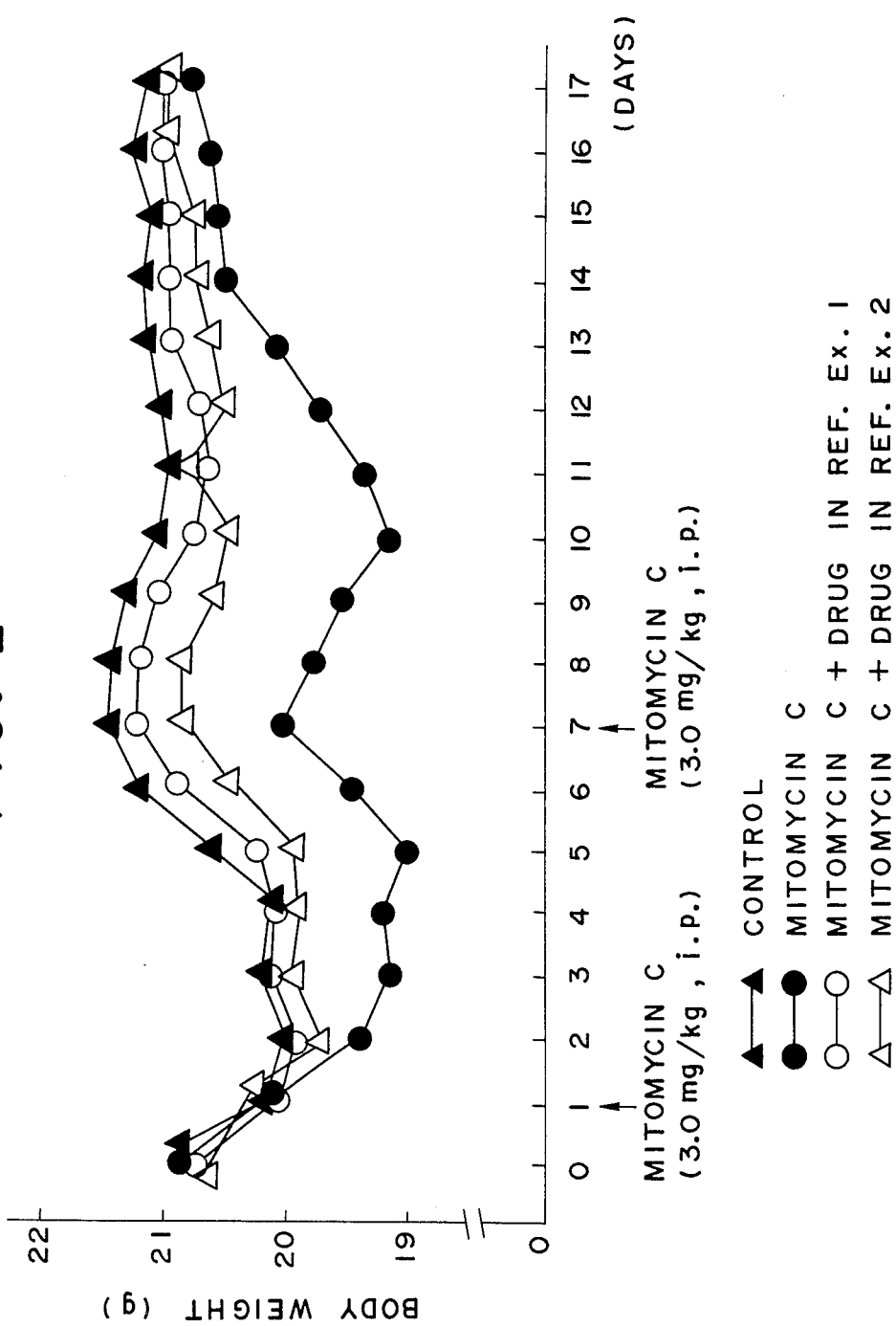

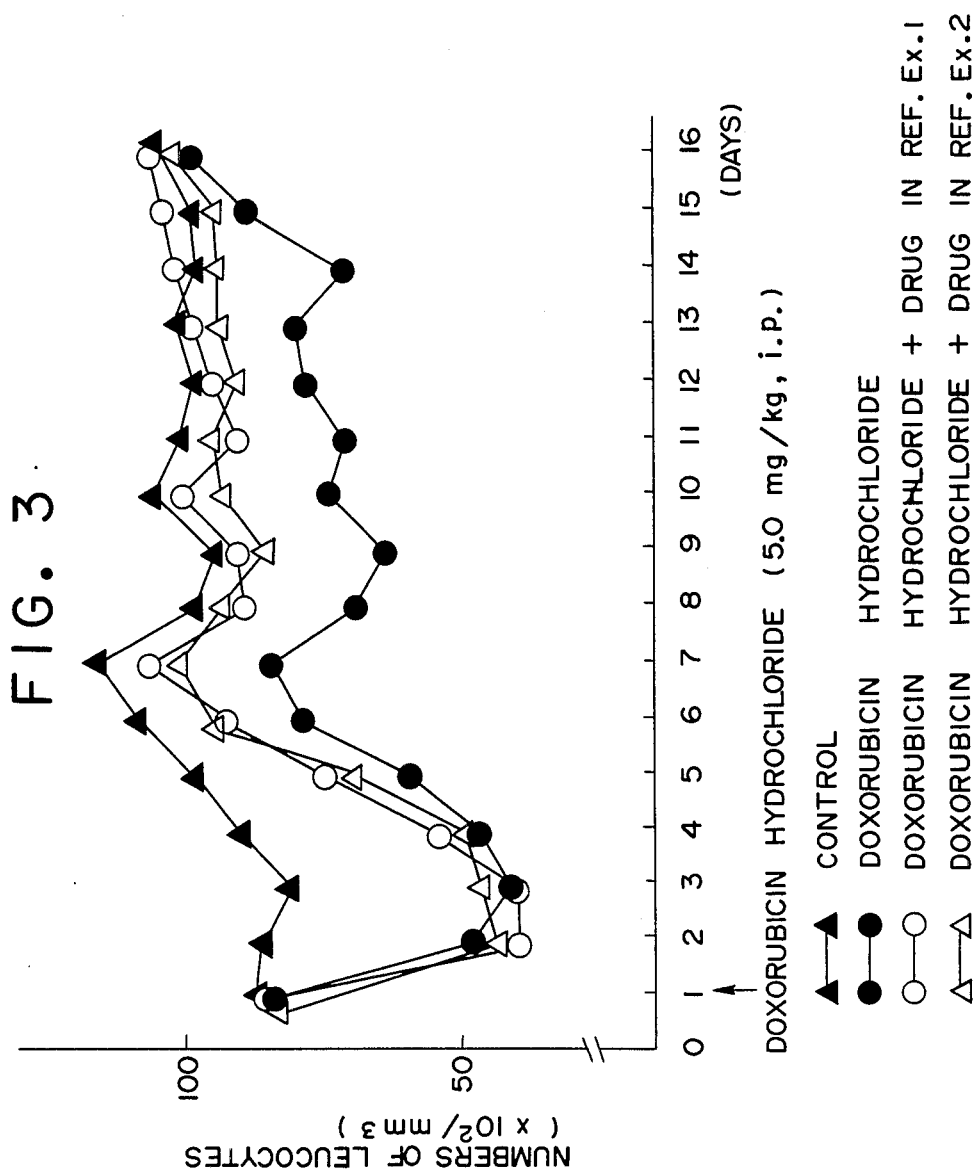

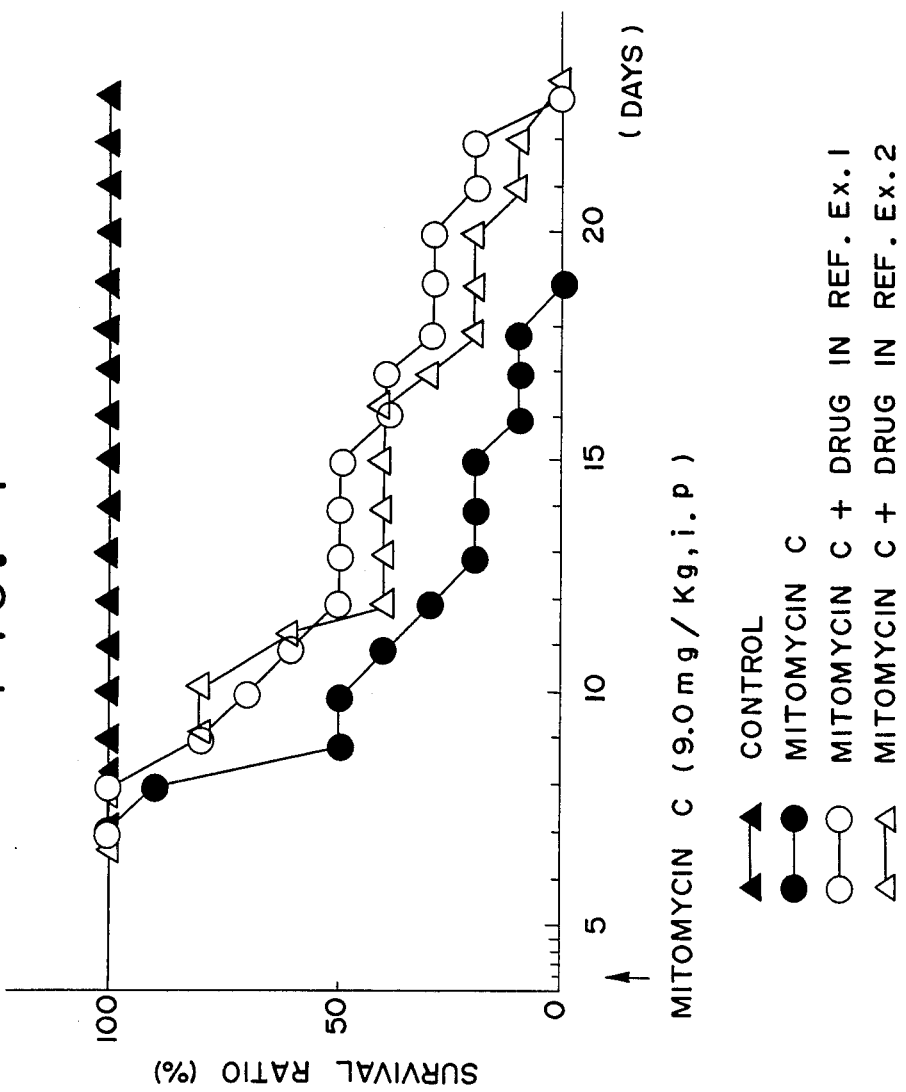

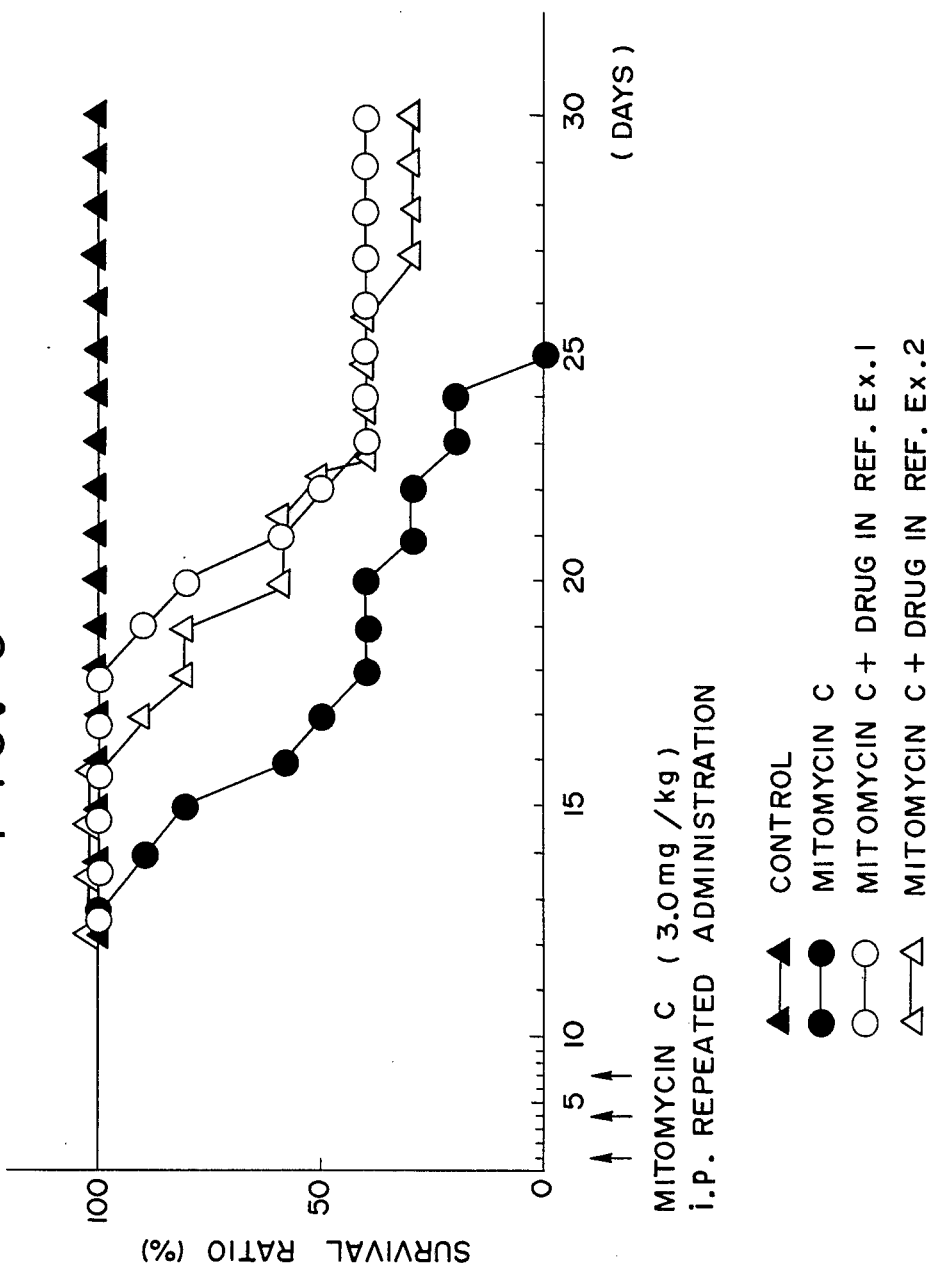

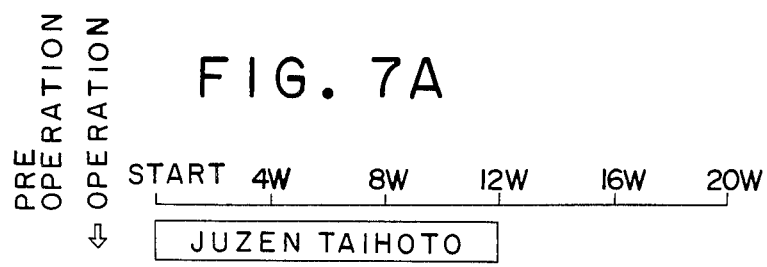
FIG. 7A
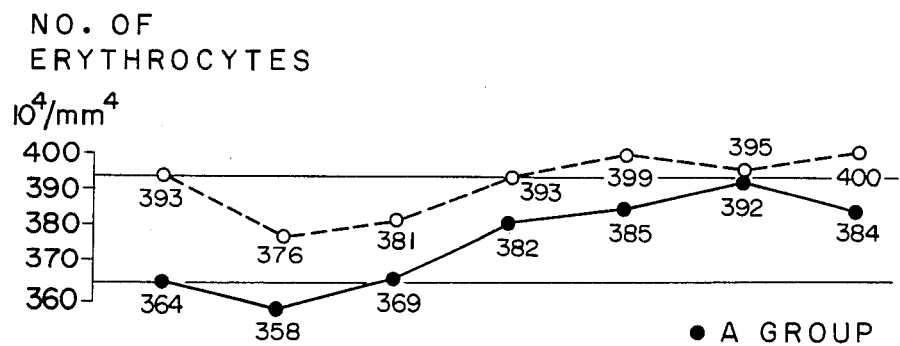
FIG. 7B
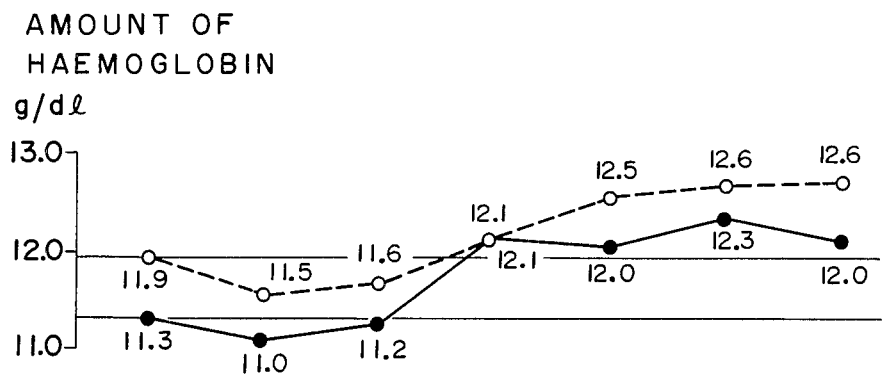

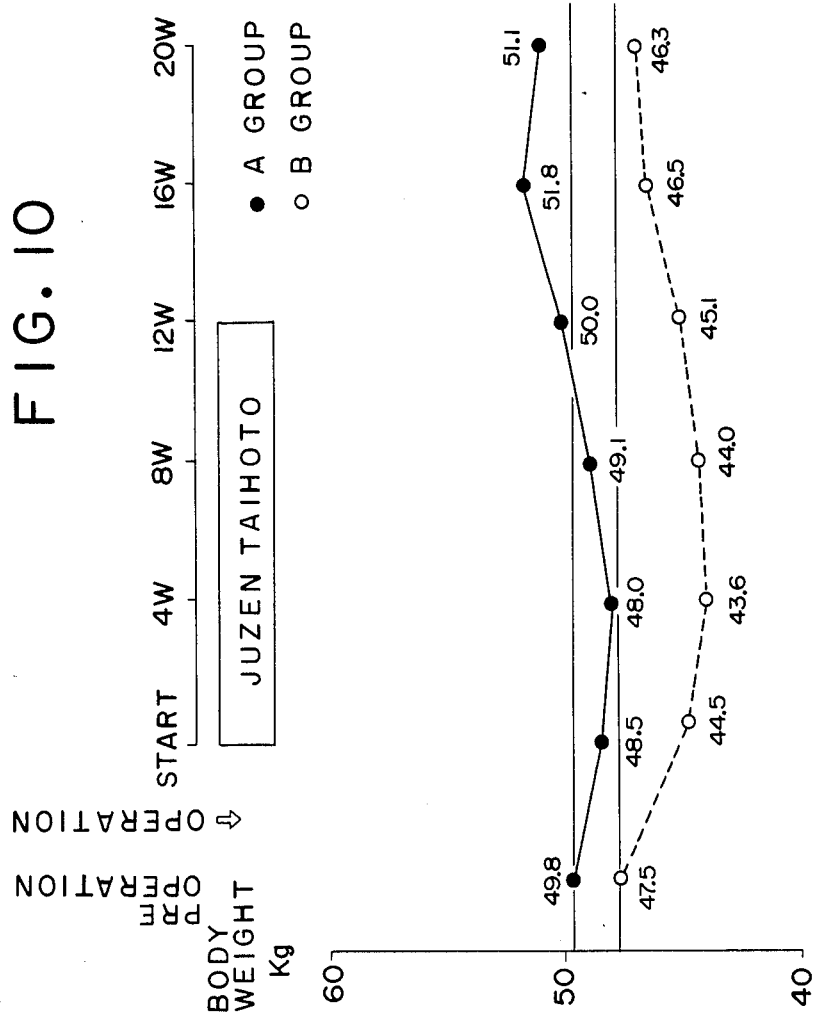

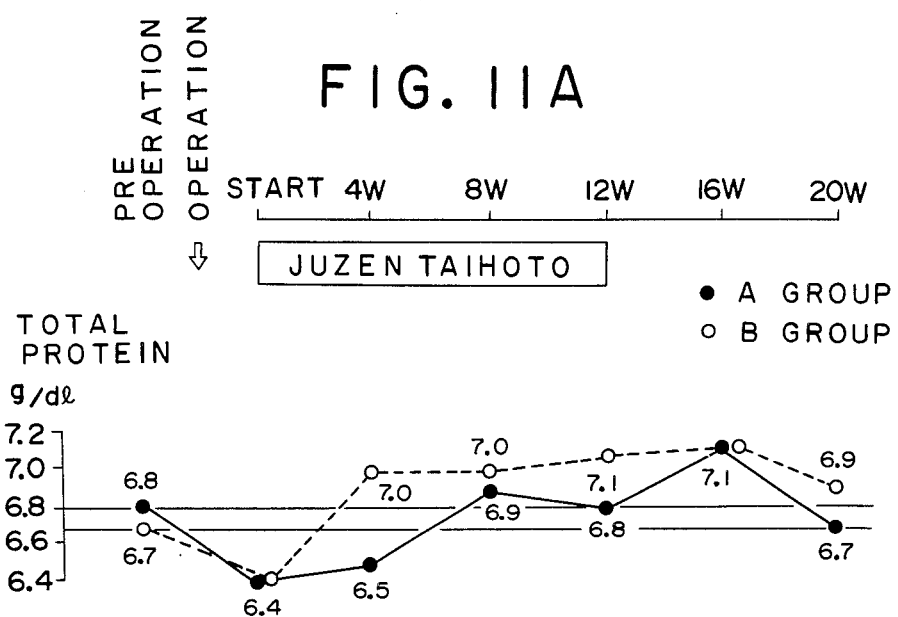
FIG. IIA
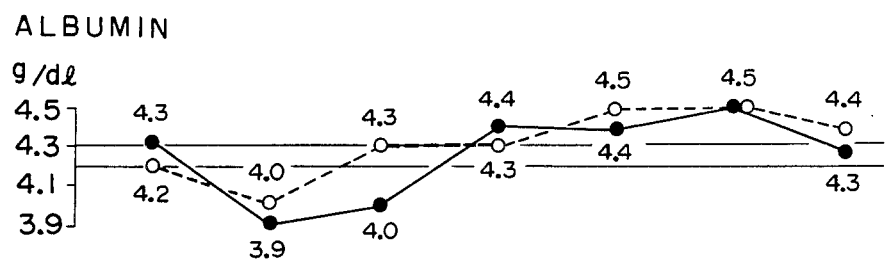
FIG. IIB

ADMINICULUM FOR ANTITUMOR AGENTS

BACKGROUND OF THE INVENTION

This invention relates to an adminiculum for use in administering mitomycin C and doxorubicin.

Mitomycin C, blue-violet crystals or crystalline powder of molecular formula $C_{15}H_{18}N_4O_5$, combines with tumor cell DNA and degrades it. It also inhibits DNA synthesis, thereby suppressing division of tumor cells. (Shibata, S. et al., Biken's J. 1, 193 (1958); Szybalski, W. et al., Proc. Nat. Acad. Sci. 50, 355 (1963)). Doxorubicin hydrochloride, orange-red colored crystalline powder of molecular formula $C_{27}H_{29}NO_{11}.HCl$, inhibits the synthetic pathway of tumor or cell DNA and inhibits division of tumor cells; in particular, it combines with DNA to inhibit RNA polymerase. (K. Tatsumi et al., GANN 65, 237 (1974)). As is well known, mitomycin C and doxorubicin hydrochloride show strong antitumor activities; however, their clinical use has to be limited due to serious side-effects, such as leukopenia and thrombocytopenia.

An object of the present invention is to provide an adminiculum for mitomycin C and doxorubicin.

Another object of the present invention is to provide an adminiculum which increases the antitumor activity of mitomycin C and doxorubicin hydrochloride while reducing the side-effects of both drugs.

DESCRIPTION OF THE INVENTION

We have found that an aqueous extract or an extract with an aqueous solution of a suitable organic solvent of mixture of crude preparations of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix will stimulate the antitumor activity of mitomycin C and doxorubicin hydrochloride and reduce their side-effects, in particular leukopenia.

Accordingly, an adminiculum for the antitumor agents mitomycin C and doxorubicin hydrochloride (hereinafter designated simply as the adminiculum of the present invention or the present adminiculum) is prepared from suitable amounts of crude preparations of Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix.

More particularly, it is preferable to use 2.0–4.0 parts by weight of Astragali radix, 2.0–4.0 parts Cinnamomi cortex, 2.0–4.0 parts Rehmanniae radix, 2.0–4.0 parts Paeoniae radix, 2.0–4.0 parts Cnidii rhizoma, 2.0–4.0 parts Atractylodis lanceae rhizoma, 2.0–4.0 parts Angelicae radix, 2.0–4.0 parts Ginseng radix, 2.0–4.0 parts Hoelen and 0.5–2.5 parts Glycyrrhizae radix.

As a preferred combination the traditional Chinese medicine (herb medicine) Juzentaihoto can be mentioned. The composition of Juzentaihoto in parts by weight is as follows:

Astragali radix: 2.5–3 parts
Cinnamomi cortex: 3 parts
Rehmanniae radix: 3 parts
Paeoniae radix: 3 parts
Cnidii rhizoma: 3 parts
Atractylodis lanceae rhizoma: 3 parts
Angelicae radix: 3 parts
Ginseng radix: 3 parts
Hoelen: 3 parts
Glycyrrhizae radix: 1.5 parts As used in the specification and claims, the "crude preparations" employed according to the invention are further defined as follows:

Astragali radix (Astragalus root)-Root of *Astragalus membranaceus* Bunge or another variety (genus Leguminosae);

Cinnamomi cortex (Cinnamon bark)-Bark (surface thereof optionally omitted) of *Cinnamomum cassia* Blume or another variety (genus Lauraceae);

Rehmanniae radix (Rehmannia root)-Root (raw or steamed) of *Rehmannia glutinosa* Liboschitz var. *purpurea* Makino or another variety (genus Scrophulariaceae);

Paeoniae radix (Peony root)-Root of *Paeonia lactiflora* Pallas (*Paeonia albiflora* Pallas var. *trichocarpa* Bunge) or related variety (genus Paeoniaceae);

Cnidii rhizoma (Cnidium rhizome)-Rhizome, usually passed through hot water, of *Cnidium officinale* Makino (genus Umbelliferae);

Atractylodis lanceae rhizoma (Atractylodes lancea rhizome)-Rhizome of *Atractylodes lancea* De Candolle or a related variety (genus Compositae);

Angelicae radix (Japanese Angelica root)-Root, usually passed through hot water, of *Angelica acutiloba* Kitagawa or a related variety (genus Umbelliferae);

Ginseng radix (Ginseng)-Root (raw or treated by passing through hot water) of *Panax ginseng* C. A. Meyer (Panax schinseng Nees) (genus Araliaceae);

Hoelen (Hoelen)—Sclerotium, outer layer deleted, of *Poria cocos* Wolf (Pachyma holen Rumph) (genus Polyporaceae);

Glycyrrhizae radix (Glycyrrhiza)-Root and stolon of *Glycyrrhiza glabra* Linne var. *glandulifera* Regel et Herder, *Glycyrrhiza uralensis* Fischer or another related variety (genus Leguminosae).

The adminiculum of the present invention can be prepared by extracting the above ten kinds of crude preparations with water or an aqueous solution comprising 5–50% v/v of a suitable water miscible organic solvent, such as an alcohol (preferably ethanol), filtering the thus-obtained extract and optionally drying by a conventional drying process, such as spray-drying, lyophilization or concentration drying. The present adminiculum can be prepared by extracting a mixture of the above ten kinds of crude preparations, or by mixing the extracts from each crude preparation. Extraction can be at room temperature or with heating, preferably at 50°–100° C.

The adminiculum of the present invention can be used as the crude extract, or in powder, granule, tablet or capsule form with conventional adjuvants or additives. The extracts can optionally be purified by conventional methods, such as dialysis or chromatography.

Preparation of the present adminiculum is exemplified in the following examples.

EXAMPLE 1

Water (285 ml) was added to a mixture of crude preparations of Astragali radix (3.0 g), Cinnamomi cortex (3.0 g), Rehmanniae radix (3.0 g), Paeoniae radix (3.0 g), Cnidii rhizoma (3.0 g), Atractylodis lanceae rhizoma (3.0 g), Angelicae radix (3.0 g), Ginseng radix (3.0 g), Hoelen (3.0 g) and Glycyrrhizae radix (1.5) and the mixture extracted at 100° C. for one hour. The extract was filtered and spray-dried to obtain a dry extract powder (2.3 g).

EXAMPLE 2

Aqueous ethanol (142.5 ml, 25% ethanol (v/v)) was added to the mixture of crude preparations as in Example 1, and refluxed at 70° C. for 30 minutes. The extract was filtered and dried to obtain a dry extract (1.9 g).

BRIEF DESCRIPTION OF THE DRAWINGS

With reference to the accompanying drawings,

FIG. 1 shows the effect of the drug preparation of leukopenia induced by mitomycin C in male $BDF_1$ mice;

FIG. 2 shows the effect of the drug preparation on body weight loss induced by mitomycin C in male $BDF_1$ mice;

FIG. 3 shows the effect of the drug preparation on leukopenia induced by doxorubicin hydrochloride in male $BDF_1$ mice;

FIG. 4 shows the effect of the drug preparation on the survival curve with single administration of mitomycin C (9 mg/kg) in male $BDF_1$ mice;

FIG. 5 shows the effect of the drug preparation on the survival curve with multiple administration of mitomycin C (3 mg/kg) in male $BDF_1$ mice;

FIG. 7 shows the number of erythrocytes and hemoglobin levels in clinical patients treated according to the invention compared with a control group;

FIG. 10 shows the body weight change in clinical patients treated according to the invention compared with a control group;

FIG. 11 shows the total protein and albumin levels in clinical patients treated according to the invention compared with a control group;

EXPERIMENTAL RESULTS

Figure 6A:
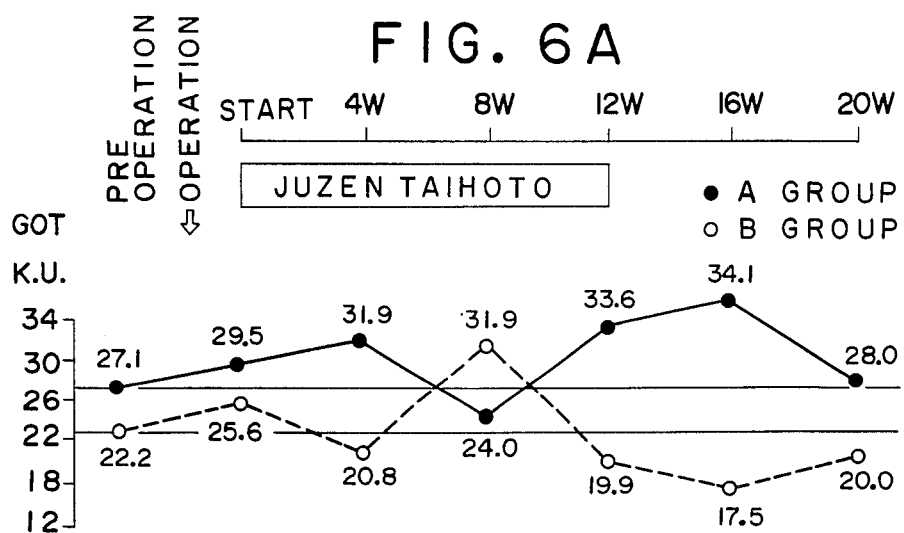
FIG. 6 shows the variation of GOT (Glutamic oxaloacetic transaminase=aspartate aminotransferase, L-aspartate: 2-oxoglutarate aminotransferase, E.C. 2.6.1.1.) and GPT (Glutamic pyruvic transaminase=alanine aminotransferase, L-alanine: 2-oxoglutarate aminotransferase, E.C. 2.6.1.2.) in clinical patients treated according to the invention compared with a control group.

The following experimental results demonstrate the effect of the present adminiculum in increasing the antitumor activity of mitomycin C and doxorubicin hydrochloride and in relieving leukopenia. Furthermore, these data show that the adminiculum of the present invention prevents or minimizes body weight loss and reduces mortality due to toxicity.

EXPERIMENT 1

Male $BDF_1$ (C57BL/6 × DBA/2) mice, age 4–4.5 weeks, were inoculated intraperitoneally with P-388 leukemia cells, $1 \times 10^6$, on day 0. The effects of the present adminiculum prepared according to Examples 1 and 2 on life prolongation were compared with mitomycin C or doxorubicin hydrochloride administered alone and in combination with an adminiculum according to the invention.

Mitomycin C (3 mg/kg) or doxorubicin hydrochloride (2.5 mg/kg) dissolved in physiological saline was administered intraperitoneally on days 1 and 7. The adminiculum obtained in Examples 1 and 2 dissolved in distilled water was administered orally, 2 g/kg/day, once a day through stomach probe, from day 1 throughout the experimental term.

Table 1 shows the effects of mitomycin C, the adminiculum obtained in Examples 1 and 2, and a combination of the adminiculum and mitomycin C on the average life-span of P-388 inoculated mice. Table 2 shows similar results using doxorubicin hydrochloride.

As shown in Tables 1 and 2, the present adminiculum per se does not show antitumor activity; however, the antitumor activities of mitomycin C and doxorubicin hydrochloride are significantly increased by therapy employing the combination according to the invention.

TABLE 1

| Treated group | Average life span (day) | T/C (%)* |
| --- | --- | --- |
| Control | 9.8 | 100 |
| Adminiculum obtained in Example 1 - (1) | 10.6 | 108 |
| Adminiculum obtained in Example 2 - (2) | 10.1 | 103 |
| Mitomycin C (MMC) | 14.4 | 147 |
| MMC + (1) | 21.0 | 214 |
| MMC + (2) | 19.8 | 202 |

*$T/C (\%) = \frac{\text{average life-span (treated)}}{\text{average life-span (control)}} \times 100$

TABLE 2

| Treated group | Average life span (day) | T/C (%)* |
| --- | --- | --- |
| Control | 11.4 | 100 |
| Adminiculum obtained in Example 1 - (1) | 11.0 | 96 |
| Adminiculum obtained in Example 2 - (2) | 11.2 | 98 |
| Doxorubicin hydrochloride (DHCl) | 18.3 | 161 |
| DHCl + (1) | 24.0 | 211 |
| DHCl + (2) | 22.4 | 196 |

*$T/C (\%) = \frac{\text{average life-span (treated)}}{\text{average life-span (control)}} \times 100$

EXPERIMENT 2

The effects of the dried extracts obtained according to Examples 1 and 2 on leukopenia and body weight loss caused by administration of mitomycin C were examined using male $BDF_1$ mice, aged 4–4.5 weeks, having a leukocyte number within the normal range.

Mitomycin C was administered, 3 mg/kg intraperitoneally, on day 1 and day 7. Extracts obtained according to Example 1 or 2 were administered, 2 g/kg/orally, from day 1 once a day for 17 days. The number of leukocytes and the body weight were measured each day throughout the experiment.

FIG. 1 shows the effect of the extracts of Examples 1 and 2 on leukopenia caused by mitomycin C. FIG. 2 shows the effect of the extracts of Examples 1 and 2 on body weight loss caused by mitomycin C. As shown in FIGS. 1 and 2, a combination of mitomycin C and the adminiculum of the present invention is effective in reducing leukopenia and body weight loss.

EXPERIMENT 3

The effects of the dried extracts obtained according to Examples 1 and 2 on leukopenia and body weight loss caused by administration of doxorubicin hydrochloride alone, 5 mg/kg intraperitoneally, were examined using male $BDF_1$ mice, aged 4–4.5 weeks, having a leukocyte number within the normal range. Preparations according to Example 1 or 2 were administered orally 2 g/kg/day, once a day throughout the experiment.

FIG. 3 shows the effects of extracts according to Examples 1 and 2 on leukopenia caused by doxorubicin hydrochloride. As shown in FIG. 3, the adminiculum of the present invention promotes recovery from leukopenia caused by doxorubicin hydrochloride.

EXPERIMENT 4

The effects of a combination of mitomycin C and the present adminiculum were examined using male $BDF_1$ mice, aged 4–4.5 weeks. Mitomycin C was administered, 9 mg/kg, intraperitoneally by single administration, or 3 mg/kg/dose, intraperitoneally in three administrations, on days 1, 4 and 7. The dried extracts according to Example 1 or 2 were administered orally 2 g/kg/day, from day 1 throughout the experiment once a day.

FIG. 4 shows the effect of the preparations according to Examples 1 and 2 on the survival curve with single administration of mitomycin C (9 mg/kg). FIG. 5 shows the effect of the drug on the survival curve with repeated administration of mitomycin C (3 mg/kg). As shown in FIG. 4 and FIG. 5, therapy using a combination of mitomycin C and the adminiculum of the present invention is effective in delaying or preventing death caused by the toxicity of mitomycin C.

The acute toxicity of the present adminiculum was examined using male ddY mice and male Wister rats. No death was observed from administering the preparations of Examples 1 and 2, 15 g/kg orally. Therefore, the present adminiculum has very low toxicity.

Considering the experimental data and the low acute toxicity, an effective dosage of the adminiculum of the present invention is, though varying dependent on the age, body weight and level of disease of the patients, generally about 2–10 g per single dosage, administered orally 3 times a day for adult. The present adminiculum can be administered separately, or prescribed together with mitomycin C or doxorubicin hydrochloride.

CLINICAL TESTS

Clinical studies of the adminiculum of the present invention was performed on patients who had undergone surgical operations for cancer. The object of the study was to investigate the effects of the present adminiculum on the recovery of constitutional power after surgery and in the prevention of the side-effects of cancer chemotherapy.

Double-blind tests using the envelop method were carried out by administering an antitumor agent with the adminiculum of the present invention (group A) and without the adminiculum of the present invention (group B, anticancer agent only).

The adminiculum was administered to the patients of group A 1–2 weeks after surgical operation for cancer, at the time when oral or rectal administration was possible, 7.5 g/day, three times a day before meals for 12 weeks. During the same period, mitomycin C and other drug therapy (bleomycin, mitomycin and/or 5-fluorouracil) were administered. Each clinical item was checked pre- and post-operation, at drug administration on day 0, and thereafter every 4 weeks for 20 weeks. The control group (group B) was monitored the same way.

Table 3 shows the number of objective cases.

TABLE 3

| Disease | group A | group B |
|---|---|---|
| cancer of the esophagus | 2 | 2 |
| stomach cancer | 4 (1) | 3 |
| valter nipple cancer | 1 | |
| pancreas cancer | | 1* |
| cancer of the colon | 1 | 2 |
| breast cancer | | 1 |
| ileus | 1 | |
| chronic pancreatitis | | 1 |
| Total | 9 (1) | 10 |

*non-erasion case ( ) = excluded case

Table 4 shows the ages of the patients.

TABLE 4

| | A (9 cases) | B (10 cases) |
|---|---|---|
| age | 53–77 | 38–83 |
| average | 64 | 61 |

Table 5 shows the sex of the patients.

TABLE 5

| | A | B |
|---|---|---|
| male | 8 | 5 |
| female | 1 | 5 |

CLINICAL EFFECTS

1. Subjective and objective symptoms (Table 6)

TABLE 6

| Symptoms | group A (9 cases) | group B (10 cases) |
|---|---|---|
| increase of appetite | 9 (100) | 7 (70) |
| reduction of languor | 8 (89) | 6 (60) |
| eruption | 2 (22) | 3 (30) |
| stomatitus | 4 (44) | 6 (60) |
| thirst | 2 (22) | 5 (50) |
| palpitation | 1 (11) | 2 (20) |
| vertigo | 1 (11) | 4 (40) |

As shown in Table 6, the patients in group A exhibited an improvement in condition relative to those of group B.

2. Body weight change (FIG. 10):

In group B, a slow increase in body weight was observed from the 4th week after operation; however, complete recovery was not observed after 20 weeks. In contrast, on the 12th week after starting the administration of the present adminiculum, recovery of body weight to the preoperation level was observed in group A. Thus, the effectiveness of the present adminiculum for reducing body weight loss induced by mitomycin C and other tumor-chemotherapeutics, such as bleomycin, mitomycin, and/or 5-fluorouracil, is observed.

3. Total protein and albumin (FIG. 11):

There was no differentiation between groups A and B in the amount of total protein and albumin.

Figure 12A:
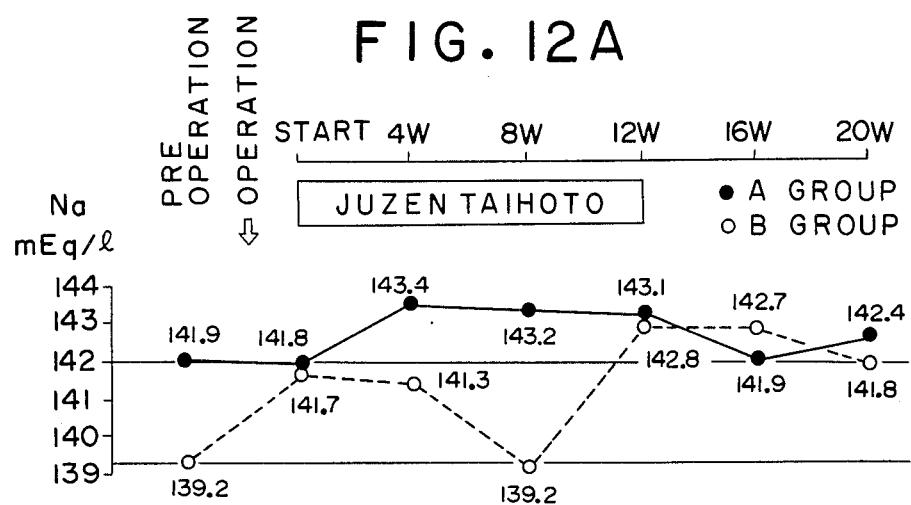
FIG. 12 shows changes in electrolyte levels in clinical patients treated according to the invention compared with a control group.
Figure 12B:
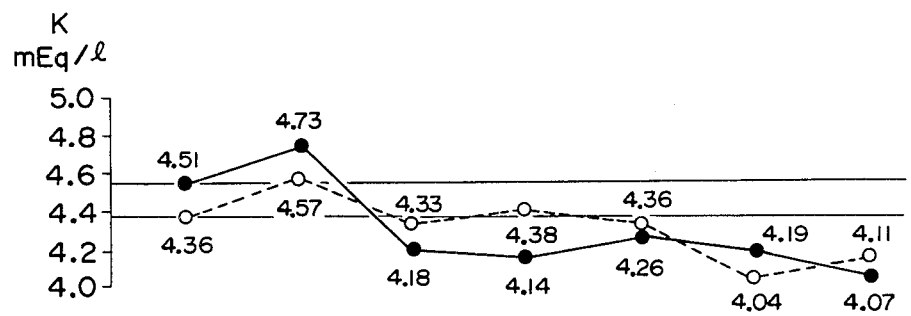

4. Change in electrolyte levels (FIG. 12):

With reference to electrolyte level, sodium was observed higher in group A, and potassium was lower.

Figure 13:
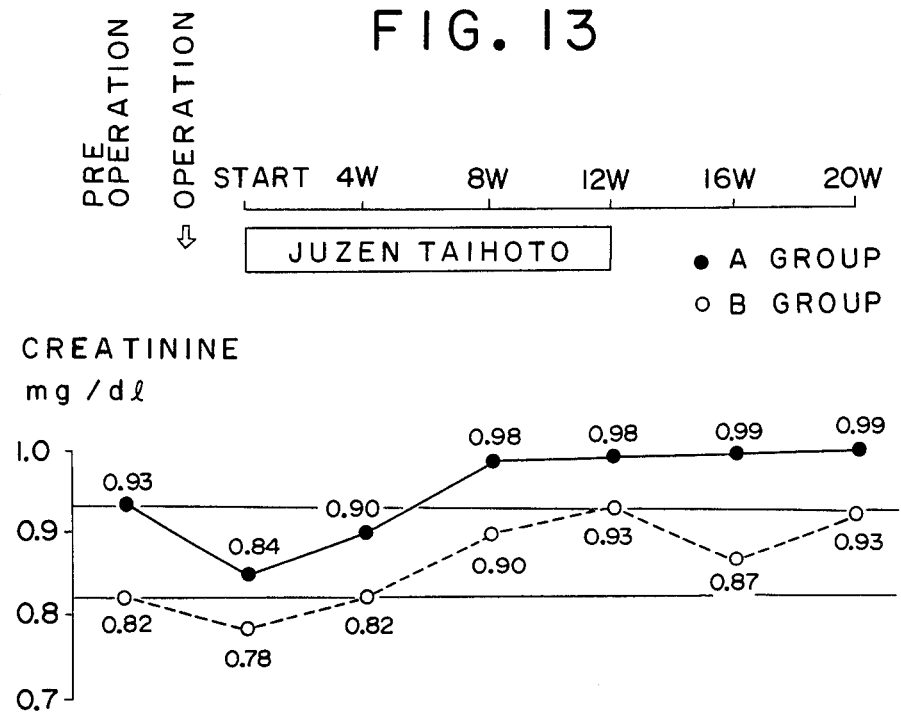
FIG. 13 shows the blood creatinine levels in clinical patients treated according to the invention compared with a control group.

5. Blood creatinine (FIG. 13):

Blood creatinine was seen to increase after operation in both groups A and B; however, no difference was observed between the groups.

Figure 6B:
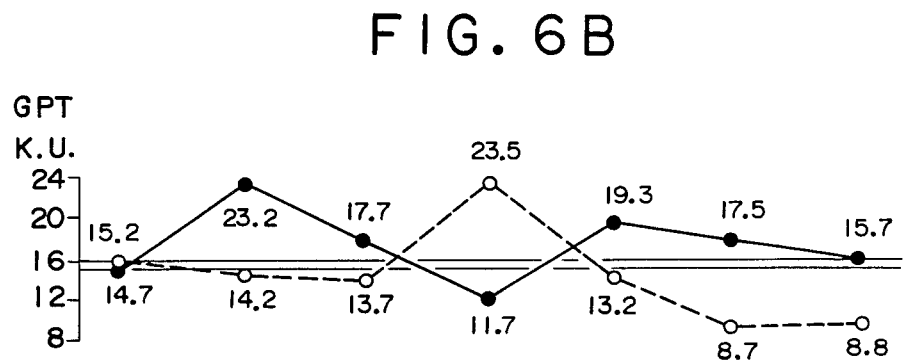

6. Variation of GOT and GPT (FIG. 6):

GOT and GPT were determined for liver function. No extreme changes were observed in either group A or B.

7. Number of erythrocytes and amount of hemoglobin (FIG. 7):

The number of erythrocytes and the amount of hemoglobin were observed to increase in both groups A and B; however, no difference was found between the groups.

Figure 8A:
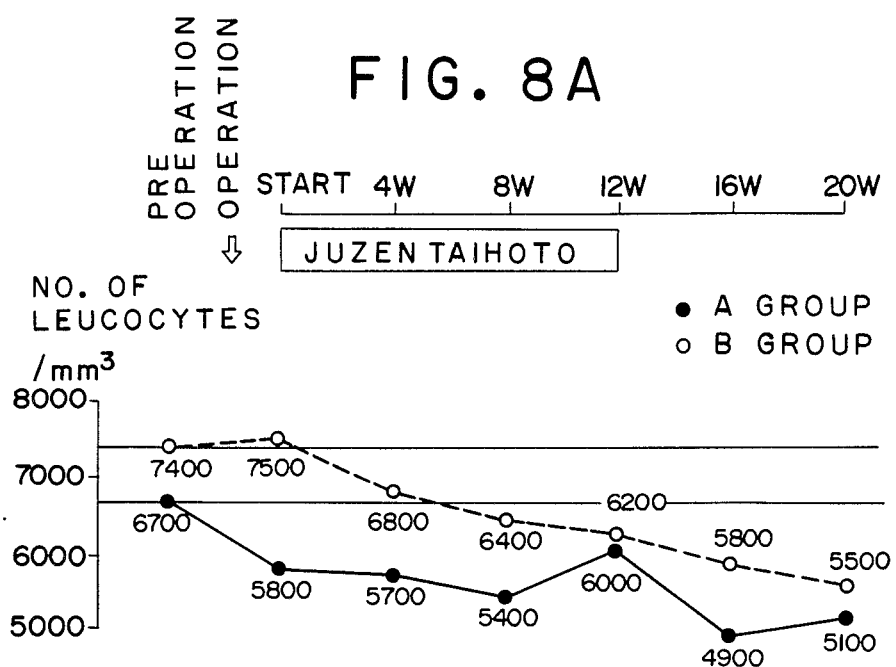
FIG. 8 shows the numbers of leukocytes and platelets in clinical patients treated according to the invention compared with a control group.
Figure 8B:
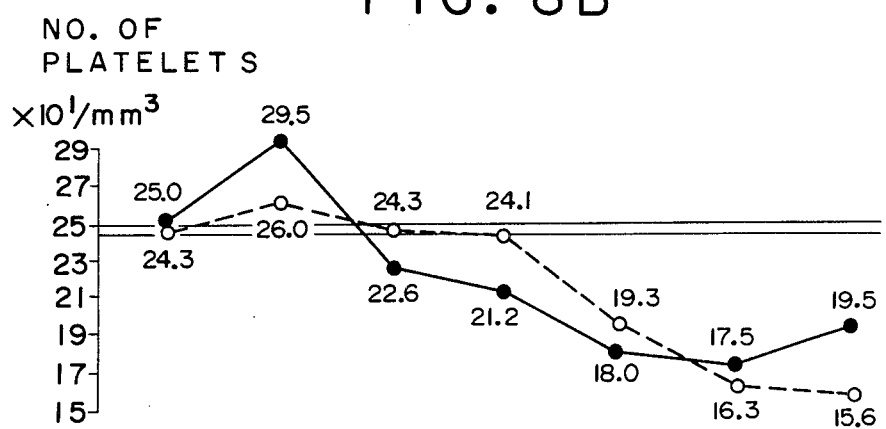

8. Number of leukocytes and platelets (FIG. 8):

The number of leukocytes in group B decreased during the administration of chemotherapeutics; a slight decrease was also observed in group A. The results seem to indicate that the administration of the adminiculum of the present invention prevents or minimizes leukopenia. No difference in platelet number was found.

Figure 9A:
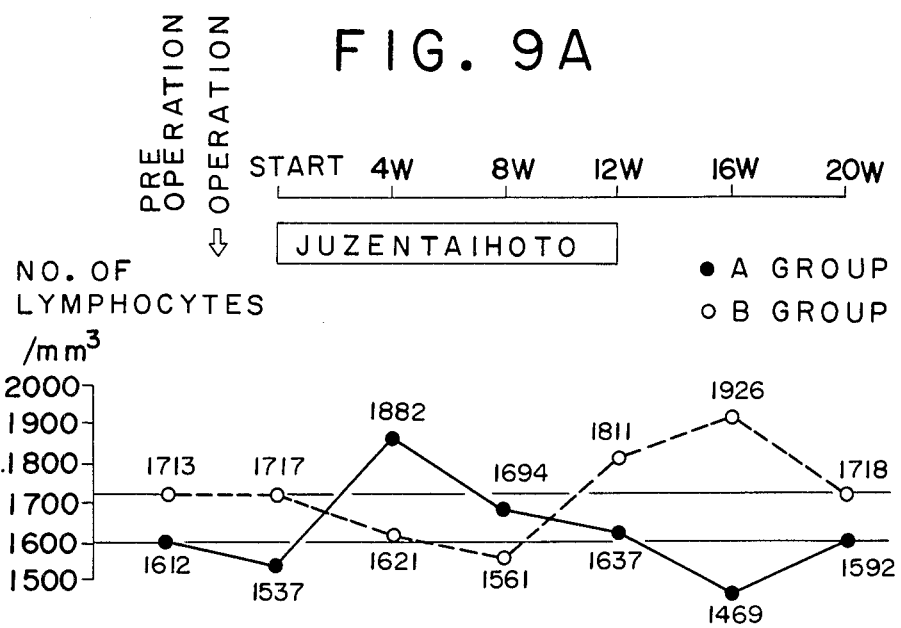
FIG. 9 shows the number of lymphocytes and gammaglobulin level in clinical patients treated according to the invention compared with a control group.
Figure 9B:
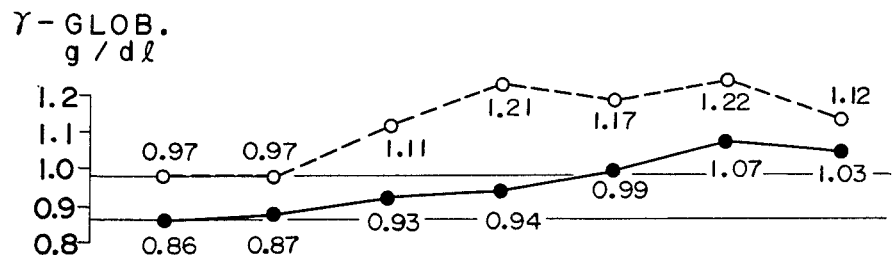

9. Number of lymphocytes and gamma-globulin (FIG. 9):

The number of lymphocytes slightly increased in group A as compared with group B. No characteristic changes were observed in gamma-globulin.

The following examples further illustrate the present invention but are not construed as limiting.

EXAMPLE 3

A preparation (200 g) produced according to Example 1 or 2 (hereinafter, "the preparation") (200 g) was mixed with lactose (89 g) and magnesium stearate (1 g). The mixture was tableted by a single tableting machine to produce slag tablets which were crushed by an oscillating machine and the granules sifted to obtain granules of 20-50 mesh.

The granules are prescribed as an adminiculum for mitomycin C or doxorubicin hydrochloride therapy at 3-15 g (corresponding to 2.07-10.34 g of the preparation of the present invention) per single dosage, 3 times a day, during the treatment term for oral administration.

EXAMPLE 4

The preparation (200 g) was mixed with fine crystalline cellulose (20 g) and magnesium stearate (5 g). The mixture was tableted by single tableting machine to produce tablets of 7 mm diameter and 225 mg weight. One tablet contains 200 mg of the preparation. 10-50 tablets are taken orally per administration, 3 times per day.

EXAMPLE 5

The preparation (500 mg) was encapsulated in a hard capsule. 4-20 capsules are administered per administration, 3 times per day.

EXAMPLE 6

The preparation (200 g) and mitomycin C (100 mg) were mixed with fine crystalline cellulose (20 g) and magnesium stearate (5 g). The mixture was tableted by single tableting machine to process tablets of 7 mm diameter and 225 mg weight. Each tablet contains 200 g of the preparation and 0.1 mg of mitomycin C. 10-30 tablets per administration were taken 3 times per day.

We claim:

1. A composition for treating tumor-bearing patients consisting essentially of (a) an effective amount of an antitumor agent selected from the group consisting of mitomycin C and doxorubicin hydrochloride and (b) an effective amount of an aqueous or aqueous organic solvent extract of a crude preparation comprising Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix, as active agents.

2. A composition for use in increasing antitumor activity of mitomycin C and for reducing side effects induced thereby consisting essentially of an effective amount of an aqueous or aqueous solvent extract of a crude preparation comprising Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix, as active agent.

3. A composition according to claim 2, wherein said crude preparation comprises 2.0-4.0 parts of Astragali radix, 2.0-4.0 parts of Cinnamomi cortex, 2.0-4.0 parts of Rehmanniae radix, 2.0-4.0 parts of Paeoniae radix, 2.0-4.0 parts of Cnidii rhizoma, 2.0-4.0 parts of Atractylodis lanceae rhizoma, 2.0-4.0 parts of Angelicae radix, 2.0-4.0 parts of Ginseng radix, 2.0-4.0 parts of Hoelen and 0.5-2.5 parts of Glycyrrhizae radix.

4. A composition according to claim 2, wherein said crude preparation comprises 2.5-3 parts of Astragali radix, 3 parts of Cinnamomi cortex, 3 parts of Rehmanniae radix, 3 parts of Paeoniae radix, 3 parts of Cnidii rhizoma, 3 parts of Atractylodis lanceae rhizoma, 3 parts of Angelicae radix, 3 parts of Ginseng radix, 3 parts of Hoelen and 1.5 parts of Glycyrrhizae radix.

5. A composition according to claim 4, wherein said crude preparation comprises 3 parts of Astragali radix.

6. A composition for use in increasing antitumor activity of doxorubicin hydrochloride and for reducing side effects induced thereby consisting essentially of an effective amount of an aqueous or aqueous solvent extract of a crude preparation comprising Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix as active agent.

7. A composition according to claim 6, wherein said crude preparation comprises 2.0-4.0 parts of Astragali radix, 2.0-4.0 parts of Cinnamomi cortex, 2.0-4.0 parts of Rehmanniae radix, 2.0-4.0 parts of Paeoniae radix, 2.0-4.0 parts of Cnidii rhizoma, 2.0-4.0 parts of Atractylodis lanceae rhizoma, 2.0-4.0 parts of Angelicae radix, 2.0-4.0 parts of Ginseng radix, 2.0-4.0 parts of Hoelen and 0.5-2.5 parts of Glycyrrhizae radix.

8. A composition according to claim 6, wherein said crude preparation comprises 2.5-3 parts of Astragali radix, 3 parts of Cinnamomi cortex, 3 parts of Rehmanniae radix, 3 parts of Paeoniae radix, 3 parts of Cnidii rhizoma, 3 parts of Atractylodis lanceae rhizoma, 3 parts of Angelicae radix, 3 parts of Ginseng radix, 3 parts of Hoelen and 1.5 parts of Glycyrrhizae radix.

9. A composition according to claim 8, wherein said crude preparation comprises 3 parts of Astragali radix.

10. A method for treating tumor-bearing patients comprising administering a composition consisting essentially of (a) an effective amount of an antitumor agent selected from the group consisting of mitomycin C and doxorubicin hydrochloride and (b) an effective amount of an aqueous or aqueous organic solvent extract of a crude preparation comprising Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix.

11. A method for increasing the antitumor activity of mitomycin C and for reducing side effects induced thereby comprising administering an effective amount of an aqueous or aqueous organic solvent extract of a crude preparation comprising Astragali radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix.

12. A method according to claim 11, wherein said effective amount is 3 dosages daily of 2–10 g per dose.

13. A method for increasing the antitumor activity of doxorubicin hydrochloride and for reducing side effects induced thereby comprising administering an effective amount of an aqueous or aqueous organic solvent extract of a crude preparation comprising Astragli radix, Cinnamomi cortex, Rehmanniae radix, Paeoniae radix, Cnidii rhizoma, Atractylodis lanceae rhizoma, Angelicae radix, Ginseng radix, Hoelen and Glycyrrhizae radix.

14. A method according to claim 13, wherein said effective amount is 3 dosages daily of 2–10 g per dose.

* * * * *